(12) United States Patent
Han

(10) Patent No.: US 6,429,646 B1
(45) Date of Patent: Aug. 6, 2002

(54) ANALOGUE EDDY DETECTING APPARATUS AND METHOD FOR CALIBRATING THE SAME

(75) Inventor: Shiquan Han, Shanghai (CN)

(73) Assignee: Baoshan Iron and Steel Corporation, Shanghai (CN)

( * ) Notice: Subject to any disclaimer, the term of this patent is extended or adjusted under 35 U.S.C. 154(b) by 0 days.

(21) Appl. No.: 09/446,698
(22) PCT Filed: Jun. 26, 1998
(86) PCT No.: PCT/CN98/00101
§ 371 (c)(1), (2), (4) Date: Apr. 6, 2000
(87) PCT Pub. No.: WO99/00665
PCT Pub. Date: Jan. 7, 1999

(30) Foreign Application Priority Data

Jun. 26, 1997 (CN) .......................... 97112564 A

(51) Int. Cl.⁷ .............................. G01R 35/00
(52) U.S. Cl. ...................... 324/202; 324/240
(58) Field of Search ................ 324/220, 221, 324/225, 237, 238, 240, 241, 242, 243, 261, 262, 525, 202, 234, 239, 601

(56) References Cited

U.S. PATENT DOCUMENTS 5,334,934 A * 8/1994 Viertl .................... 324/220

FOREIGN PATENT DOCUMENTS

CN A2194002 4/1995
CN A1114747 1/1996

* cited by examiner

Primary Examiner—Jay Patidar
(74) Attorney, Agent, or Firm—Birch, Stewart, Kolasch & Birch, LLP

(57) ABSTRACT

The invention relates to a method for calibrating the initial sensitivity of the eddy current roll-flaw detecting apparatus and an eddy current roll-flaw detecting apparatus which can be calibrated by the method. The method comprises the following steps: a) detecting an artificial defect sample to obtain a first vector; b) generating an analogue artificial defect signal; c) adjusting the analogue artificial defect signal to make it equal the first vector; and d) inputting the analogue artificial defect signal into the eddy current roll-flaw detecting apparatus, and adjusting the eddy current roll-flaw detecting apparatus to enable it to give a warning, wherein steps a) and c) are both implemented by means of the impedance analyzing unit having the function of displaying the impedance vector built in the eddy current roll-flaw detecting apparatus. The eddy current roll-flaw detecting apparatus comprises an impedance analyzing unit having the function of displaying the impedance vector, a modulation analyzing circuit and a warning circuit.

6 Claims, 2 Drawing Sheets

ANALOGUE EDDY DETECTING APPARATUS AND METHOD FOR CALIBRATING THE SAME

This application is the national phase under 35 U.S.C. §371 of PCT International Application No. PCT/CN98/00101 which has an International filing date of Jun. 26, 1998 which designated the United States of America.

FIELD OF THE INVENTION

The present invention relates to an analogue method for calibrating the initial sensitivity of the non-destructive flaw-detecting apparatus, especially the eddy current roll-flaw detecting apparatus, and to a non-destructive flaw-detecting apparatus, especially an eddy current roll-flaw detecting apparatus, whose initial sensitivity can be calibrated by the method.

BACKGROUND OF THE INVENTION

In a rolling mill, the roll is the main consumable part. After being used for a period of time, cracks and hardness abnormalities (hereinafter referred to collectively as "flaw") may occur on the surface of the roll, which, if not found and repaired in good time, may cause serious spalling of the roll body or even break the roll. Generally, to prevent such a case from happening, the roll is regularly detected by means of an eddy current roll-flaw detecting apparatus. The conventional eddy current roll-flaw detecting apparatus comprises an impedance analyzing unit, a modulation analyzing circuit and a warning circuit. In order to effectively detect the flaws of the roll, the initial sensitivity of the eddy current roll-flaw detecting apparatus should be calibrated. CN 1114747 A (laid open on Jan. 10, 1996) disclosed such a calibrating method, comprising the following steps: detecting an artificial defect sample by means of a computer-based eddy current flaw detector to obtain a first vector; attaching the detecting probe of the computer-based eddy current flaw detector to the output terminal of an analogue artificial defect signal generator to obtain a second vector, and adjusting the attenuator and the phase shifter of the analogue artificial defect signal generator in such a way that the second vector equals the first vector; attaching the output terminal of the analogue artificial defect signal generator to the probe of the eddy current roll-flaw detecting apparatus, and adjusting the modulation frequency of the analogue artificial defect signal generator and the gain of the eddy current roll-flaw detecting apparatus to enable it to give a warning.

The disadvantage of the above known method for calibrating the initial sensitivity of the eddy current roll-flaw detecting apparatus is that the precision of calibration is low. This is because the detecting means used in the calibration procedure is different from that used in actual detection; in the former case, a computer-based eddy current flaw detector which is separated from the eddy current roll-flaw detecting apparatus is used and, in the latter case, the impedance analyzing unit built in the eddy current roll-flaw detecting apparatus is used. The output powers of the two detecting means are different and the impedances of them can not be matched easily.

SUMMARY OF THE PRESENT INVENTION

The object of the invention is to provide a method for calibrating the initial sensitivity of the eddy current roll-flaw detecting apparatus with high precision, and an eddy current roll-flaw detecting apparatus, whose initial sensitivity can be calibrated by the method.

According to the invention, the method for calibrating the initial sensitivity of the eddy current roll-flaw detecting apparatus comprises the following steps: a) detecting an artificial defect sample to obtain a first vector; b) generating an analogue artificial defect signal; c) adjusting the analogue artificial defect signal to make it equal the first vector; and d) inputting the analogue artificial defect signal, which has been adjusted, into the eddy current roll-flaw detecting apparatus, and adjusting the eddy current roll-flaw detecting apparatus to enable it to give a warning, wherein steps a) and c) are both implemented by means of the impedance analyzing unit having the function of displaying the impedance vector built in the eddy current roll-flaw detecting apparatus.

The eddy current roll-flaw detecting apparatus according to the invention comprises: an impedance analyzing unit having the function of displaying the impedance vector, thereby displaying the first vector and the analogue artificial defect signal; a modulation analyzing circuit; and a warning circuit.

In accordance with the method of the invention, the same detecting means, i.e., the impedance analyzing unit as one of the components of the eddy current roll-flaw detecting apparatus, is used in both of the calibration procedure and actual detection. Therefore, the disadvantage of the prior art caused by the use of two different detecting means as stated above can be overcome, and a much higher precision of calibration can be achieved.

Since the impedance analyzing unit of the eddy current roll-flaw detecting apparatus of the invention has the function of displaying impedance vectors, the initial sensitivity of the apparatus can be calibrated by the method of the invention. Therefore, the precision of detection of the apparatus of the invention can be increased enormously.

DETAILED DESCRIPTION OF THE PREFERRED EMBODIMENT

In the following, the invention will be described in detail with reference to the accompanying drawings.

Figure 1:
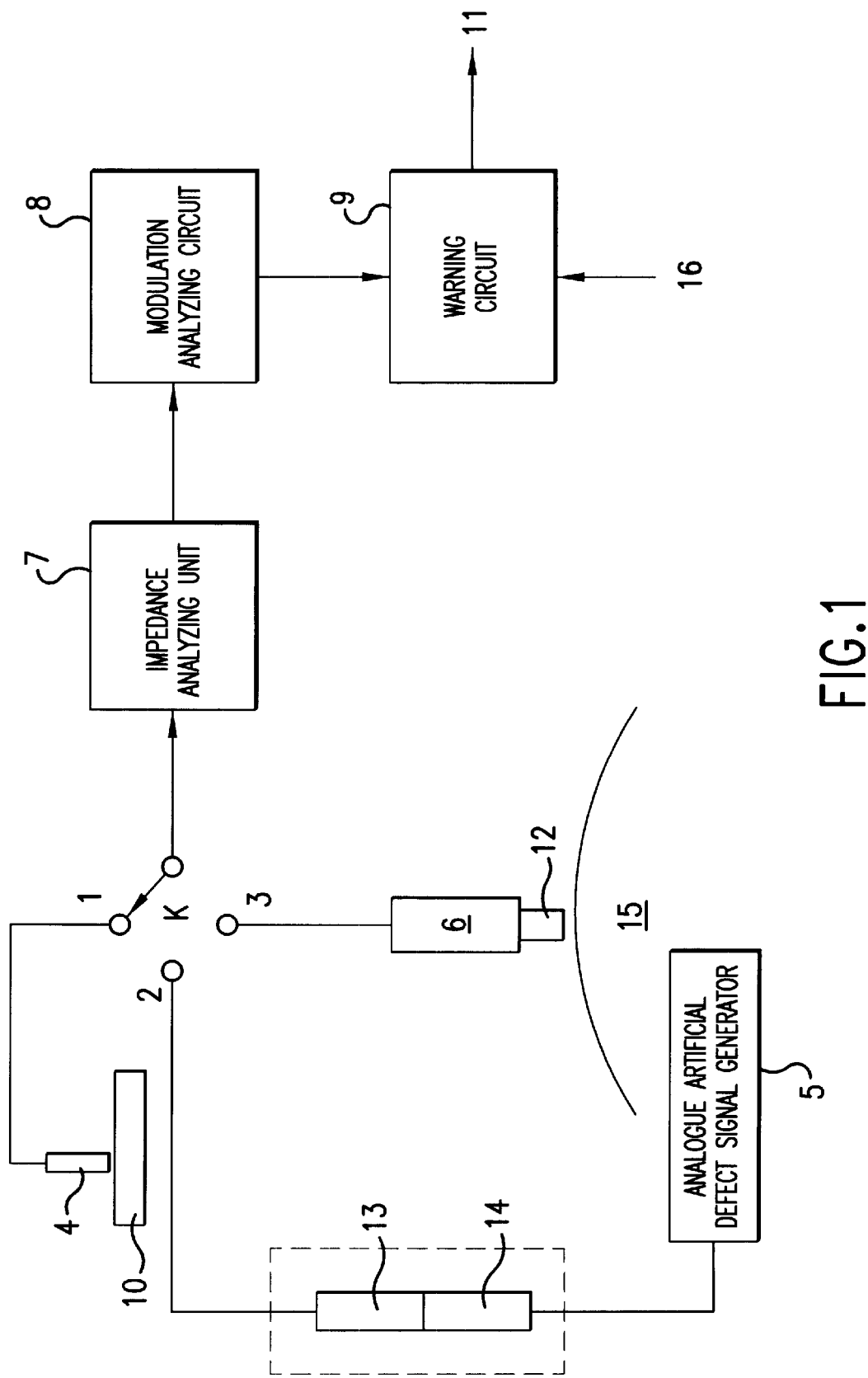
FIG. 1 is the schematic diagram of the eddy current roll-flaw detecting apparatus of the invention.

Referring to FIG. 1, according to an preferred embodiment of the invention, the eddy current roll-flaw detecting apparatus comprises: an impedance analyzing unit having the function of displaying the impedance vector 7, a modulation analyzing circuit 8 and a warning circuit 9. As the impedance analyzing unit 7, the Smart All-Digital Multiple-Purpose Eddy current Flaw Detector EEC-20, manufactured by Anderson (Xiamen) Electronics Co. Ltd., can be used. Because the impedance analyzing unit 7 has the function of displaying the impedance vector, all of the flaw information picked up by the probe of the eddy current roll-flaw detecting apparatus during the calibration procedure can be stored to facilitate the comparison of the first vector and the analogue artificial defect signal. Through a switch K, the impedance analyzing unit 7 can be connected to a probe 4 used to detect an artificial defect sample 10 (position 1), a probe 13 used to detect the output signal of an analogue artificial defect signal generator 5 (position 2), and an actual detection probe 12 (position 3), respectively. The actual detection probe 12 is installed on a slider 6 which is controlled by a stepmotor, an elevating mechanism and a sensor. By means of the slider 6, the surface of a roll 15 can be scanned by the actual detection probe 12 in actual detection.

Figure 2:
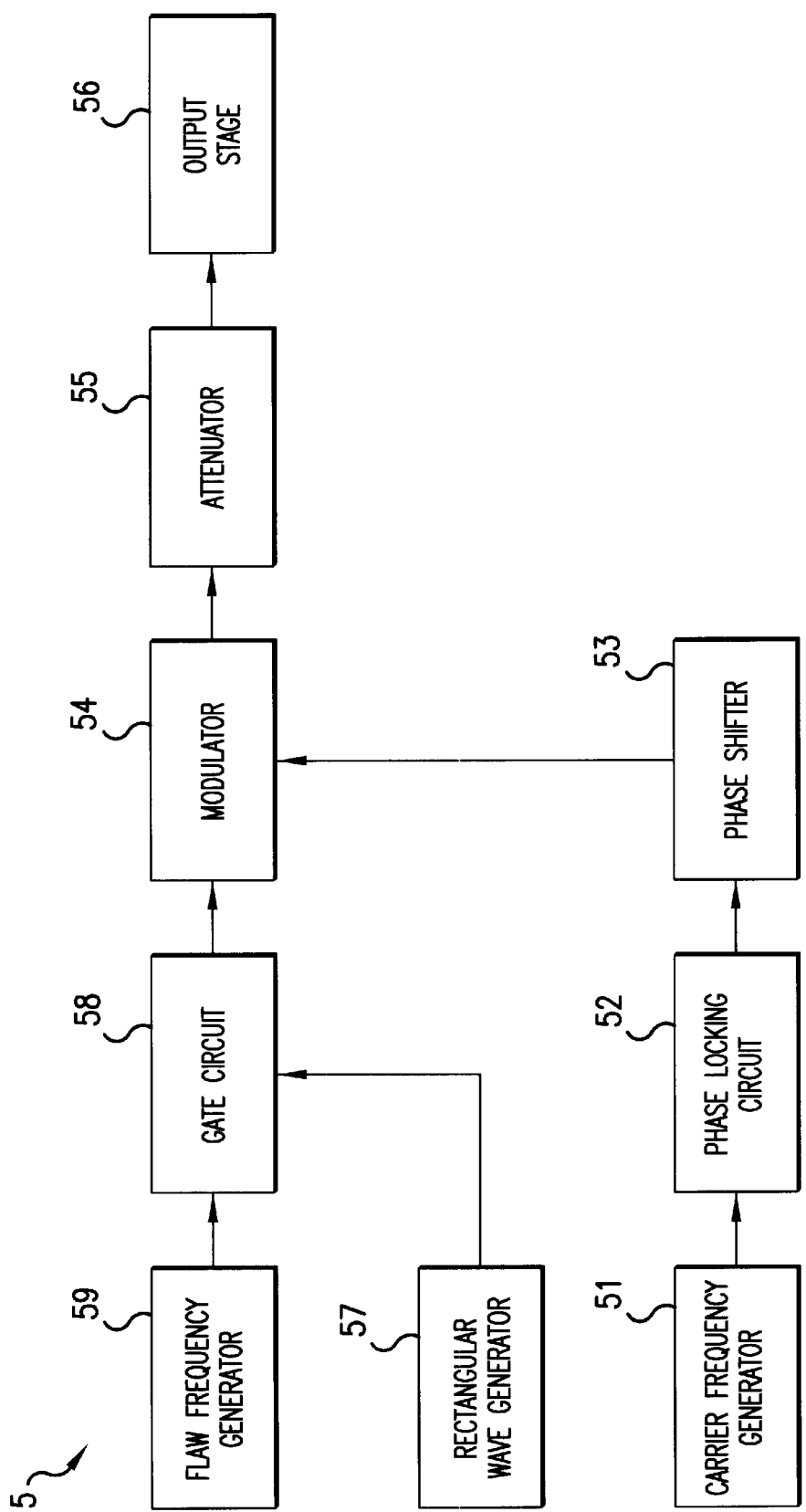
FIG. 2 is the block diagram of the analogue artificial defect signal generator according to the invention showing in detail the elements that comprise element 5 in FIG. 1.

The analogue artificial defect signal generator 5 is used to generate a simulated vector signal representative of a roll flaw under a certain roll speed, which can be adjusted to be equal to the analogue signal obtained by detecting the artificial defect sample 10. As illustrated in FIG. 2, the analogue artificial defect signal generator 5 comprises a carrier frequency generator 51, a phase locking circuit 52, a phase shifter 53, a modulator 54, an attenuator 55, an output state 56, a rectangular wave generator 57, a gate circuit 58 and a flaw frequency generator 59. The analogue artificial defect signal generator 5 operates in the following way: a continuous, unmodulated carrier frequency generated by an oscillator is inputted into and shaped by the carrier frequency generator 51, and then so adjusted by the phase locking circuit 52 and the phase shifter 53 that a desired phase and a desired amplitude can be obtained. An modulation frequency generated by the flaw frequency generator 59 is supplied to the modulator 54, which generates the simulated vector signal for the purpose of calibration. The simulated vector signal is outputted from the output stage 56, FIG. 2, to the output terminal 14 and probe 13 of FIG. 1.

Preferably, to further increase the precision of calibration, the probe 4 used to detect an artificial defect sample, the probe 13 used to detect the output signal of the analogue artificial defect signal generator, and the actual detection probe 12 may have identical parameters, including the shape, the turn and the core characteristics of the probe coil. In addition, the probe 13 and the output terminal 14 of the analogue artificial defect signal generator 5 can be fixedly coupled together by means of, for example, resin, to avoid errors which would be caused by manual coupling.

The initial sensitivity of the eddy current roll-flaw detecting apparatus is calibrated as follows. First, turn the switch K to position 1, and detect the artificial defect sample 10 through the probe 4 of the impedance analyzing unit 7, obtaining a first vector on the display of the impedance analyzing unit 7. The sample 10 is prepared by making an artificial defect (a groove, a hardness abnormality and the like) according to certain process specifications on a block which is cut from the surface-undefected portion of a defected roll, or from the working surface portion of the remainder left in manufacturing new rolls. Then, turn the switch K to position 2, and adjust the amplitude and phase of the output signal of the analogue artificial defect signal generator 5, to make the output signal equal the first vector. Then, adjust the modulation frequency of the analogue artificial defect signal generator 5 to make it consistent with the frequency of the modulation analyzing circuit 8, and adjust the gain of the warning circuit 9 to enable it to give a warning. Once the calibration procedure is completed, turn the switch K to position 3, and the actual detection of roll 15 can be begun through the actual detection probe 12.

What is claimed is:

1. A method for calibrating the initial sensitivity of the eddy current roll-flaw detecting apparatus, comprising the following steps:
   switchably connecting an impedance analyzing unit to a first probe associated with an artificial defect sample;
   detecting a defect in the artificial defect sample to obtain and store a first impedance vector in the impedance analyzing unit;
   switchably connecting the impedance analyzing unit to a second probe connected to a analogue artificial defect signal generator;
   detecting an second impedance vector outputted by said analogue artificial defect signal generator, and adjusting an amplitude and a phase of said second impedance vector to match said first impedance vector, wherein said second impedance vector is outputted from the impedance analyzing unit to a modulation-analyzing circuit;
   adjusting a modulation frequency of the second impedance vector to be consistent with a frequency of the modulation-analyzing circuit; and
   when they are consistent, adjusting a gain of a warning circuit attached to an output side of the modulation analyzing unit to give a warning, thereby completing an initial calibration procedure of the eddy current roll-flaw detecting apparatus.

2. A method for calibrating the initial sensitivity of the eddy current roll-flaw detecting apparatus according to claim 1, wherein an output terminal of the analogue artificial defect signal generator is fixedly coupled to the second probe.

3. A method for calibrating the initial sensitivity of the eddy current roll-flaw detecting apparatus according to claim 1, wherein the eddy current roll-flaw detecting apparatus comprises an actual detection probe, and the first probe, the second probe and the actual detection probe have identical parameters.

4. An eddy current roll-flaw detecting apparatus, comprising:
   an impedance analyzing unit alternatively connectable by means of a switch to any one of:
      an artificial defect sample having a defect condition detectable via a first probe;
      an analogue artificial defect signal generator capable of generating a second impedance vector, said second impedance vector being detectable via a second probe; and
   an actual detection probe for detecting defects in an actual roll, wherein:
      the impedance analyzing unit for obtaining, storing, displaying, and comparing an impedance vector obtained from any of said probes, and wherein:
         the analogue artificial signal generator is adjustable by an operator for adjusting the second impedance vector obtained from the analogue artificial signal generator to be equal to a first impedance vector obtained from the artificial defect sample via the first probe;
         a modulation-analyzing circuit connected to an output side of the impedance analyzing unit for enabling the operator to view the second impedance vector generated by the analogue artificial signal generator, and providing for comparing and adjusting it to be consistent with a frequency of the modulation-analyzing circuit; and
         a warning circuit attached to an output side of the modulation-analyzing circuit, wherein during an initial calibration process, a gain of the warning circuit is adjusted to give a warning when the first impedance vector is consistent with the second impedance vector, thereby completing an initial calibration of the eddy current roll-flaw detecting apparatus, and providing for an improved precision for detecting a flaw in the actual roll.

5. An eddy current roll-flaw detecting apparatus according to claim 4, wherein an output terminal of the analogue artificial defect signal generator is fixedly coupled to the second probe.

6. An eddy current roll-flaw detecting apparatus according to claim 4, wherein the first probe, the second probe and the actual detection probe have identical parameters.

* * * * *